United States Patent [19]

Forward et al.

[11] 3,966,863

[45] June 29, 1976

[54] ORAL HYGIENE COMPOSITIONS

[75] Inventors: Geoffrey Charles Forward, Redhill; Susan Ann Duke, Croydon; Melissa Anne Bell, New Malden, all of England

[73] Assignee: Beecham Group Limited, United Kingdom

[22] Filed: Dec. 4, 1974

[21] Appl. No.: 529,567

[52] U.S. Cl. .................................. 424/52; 424/49
[51] Int. Cl.² ........................................ A61K 7/18
[58] Field of Search ........................... 424/49–52

[56] References Cited
UNITED STATES PATENTS

| | | | |
|---|---|---|---|
| 3,574,823 | 4/1971 | Roberts et al. | 424/49 |
| 3,711,604 | 1/1973 | Colodney et al. | 424/52 |

*Primary Examiner*—Lewis Gotts
*Assistant Examiner*—Cary Owens

[57] ABSTRACT

Oral hygiene compositions of enhanced anti-cariogenic activity such as toothpaste containing a calcium carbide abrasive and a combination of an ionic fluoride and an ionic monofluorophosphate in amounts to provide, respectively, from 40–80% and 20–60% of the total fluorine content of the composition.

8 Claims, No Drawings

ORAL HYGIENE COMPOSITIONS

This invention relates to oral hygiene compositions having anti-cariogenic activity.

In the past few years many proposals have been made to incorporate a wide variety of fluoride compounds into oral hygiene compositions such as dentifrices in order to provide them with anti-cariogenic activity. This activity is believed to result from the effect that the fluoride compound has in reducing the solubility of tooth enamel in a weakly acid media such as often occurs in the mouth as the result of the action of bacteria on foods. The effect of reducing the solubility of dental enamel is believed to result from an interaction of hydroxyapatite, that is the mineral which constitutes the major part of dental enamel, with the fluoride to produce fluoroapatite. This is because the solubility of reducing effect increases with increasing fluoride content of the hydroxyapatite. However, fluoride uptake is obviously not the only criterion because whilst more fluorine is taken up into the hydroxyapatite mineral of the teeth when sodium fluoride, rather than sodium monofluorophosphate, is used, the sodium monofluorophosphate results (at the same level of incorporation of fluorine) in a greater reduction in the solubility of the tooth enamel.

While sodium fluoride was one of the first fluorides advocated for its addition to dentrifices, it has found relatively little use because it has long been believed that the calcium-containing abrasives often used in dentifrices, especially calcium carbonate, are incompatible with ionic fluorides such as sodium fluoride. Thus it was long ago reported that the anti-cariogenic effect of sodium fluoride was inhibited by the presence of calcium carbonate, no doubt because it was believed that these substances would primarily interact to produce the insoluble and inactive calcium fluoride. For this reason also the use of sodium fluoride as an anti-cariogenic agent in oral hygiene compositions has not found favor in recent years, sodium monofluorophosphate has often been used instead.

Surprisingly, we have now found that the inactivation of sodium fluoride by calcium carbonate is not absolute but occurs only up to a threshold concentration of the sodium fluoride. Equally surprisingly, we have found that an enhanced anticariogenic effect is obtained in oral dentrifice compositions comprising a calcium carbonate abrasive if these contain a mixture of an ionic fluoride and an ionic monofluorophosphate. We have found that this enhanced effect is significant when from 40–80%, preferably 40–55% of the fluoride content of the composition has been introduced as an ionic fluoride and from 20–60%, preferably 45–60% has been introduced as an ionic monofluorophosphate.

Accordingly, the present invention provides an oral hygiene composition comprising: (a) a calcium carbonate abrasive; (b) an ionic fluoride; and (c) an ionic monofluorophosphate, the weights of the said ingredients (b) and (c) being sufficient to provide respectively from 40–80% and 20–60% of the total fluorine content of the composition.

The ionic fluoride is one capable of producing fluoride ions in aqueous solution. Preferably there is employed an alkali-metal fluoride such as sodium, potassium or lithium fluoride; the use of sodium fluoride is especially preferred. Other suitable fluorides include ammonium, stannous and zinc fluorides.

Likewise the ionic monofluorophosphate is preferably an alkali metal monofluorophosphate. Sodium monofluorophosphate, $NaHPO_3F$, is especially preferred, but the corresponding potassium and/or lithium salts can also be employed. Also the term "monofluorophosphate" as used herein includes reference to monofluoropolyphosphates, such as those of the formulae $Na_4P_3O_9F$; $K_4P_3O_9F$; $Na_3KP_3O_9F$; $(NH_4)_3NaP_3O_9F$ and $Li_4P_3O_9F$.

The total amount of fluoride and monofluorophosphate used is dependent to some extent on the type of dentifrice composition, but it should be an effective, but non-toxic, amount. Typically the fluoride and monofluorophosphate are present in the oral hygiene composition in an amount to provide a total of from 0.025% to 0.2% of fluorine based on the weight of the oral hygiene composition. The preferred total fluoride level is from 0.05–0.12% by weight of the composition. Also, preferably the fluoride and fluorophosphate provide respectively 40–55% and 45–60% of the total fluorine content.

The oral hygiene compositions of the invention also comprise a dental abrasive which consists of or comprises calcium carbonate in an abrasive form. Such calcium carbonate can be in either of the geological forms known as Aragonite and Calcite or a mixture of the two. The preferred forms are synthetically precipitated chalks, particularly waterworks chalk, which is that precipitated from hard water by lime. Other forms of calcium carbonate include powdered limestone and milled marble or mined powder products. Preferably the calcium carbonate should have a weight median diameter of less than 40 microns.

Other dental abrasives may also be present in admixture with the calcium carbonate.

For instance there may be employed water-insoluble sodium or potassium metaphosphates, hydrated or anhydrous dicalcium phosphate, calcium pyrophosphate, zirconium silicate or mixtures thereof. Particularly useful polishing agents are various forms of silica, especially silica xerogels as defined in U.S. Pat. No. 3,538,230, though such xerogels may have an average particle size diameter up to 50 microns. The abrasive(s) may be employed in a total amount of from 10 to 99% by weight of the composition of the invention. Prferably such compositions are in the form of dentifrice pastes containing 20 to 75% of dental abrasive, though they can be in the form of powders containing 70 to 99% of the abrasive. If desired, the compositions of the invention can be formulated as cored or striped dentifrice compositions, particularly with an opaque core or strips (containing the calcium carbonate abrasive) within or on a transparent gel. The gel can contain one or more of the fluorine-containing ingredients and in such cases the composition is taken as a whole in determining proportions of ingredients as aforesaid.

The oral hygiene compositions of the invention will also usually contain surfactants, gelling agents and other excipients such as flavouring and colouring agents.

The surfactant is normally a water-soluble non-soap or synthetic organic detergent. Suitable surfactants include the water-soluble salts of: higher fatty acid monoglyceride monosulphates (for example sodium hydrogenated coconut fatty acid monoglyceride monosulphate); higher alkyl sulphates (for example sodium lauryl sulphate); alkylarylsulphonates (for example sodium dodecylbenzenesulphonates); and higher alkyl sulphoacetates (for example sodium lauryl sulphoacetate). There may also be used the saturated higher aliphatic acyl amides of lower aliphatic amino carboxylic acids having 12 to 16 carbon atoms in the acyl radical and in which the amino acid portion is derived from the lower aliphatic saturated monoaminocarboxylic acids having 2 to 6 carbon atoms, such as the fatty acid amides of glycine, sarcosine, alanine, 3-aminopropanoic acid and valine, particularly the N-lauroyl, myristoyl and palmitoyl sarcosinate compounds. Conventional non-ionic surfactants may also be included if desired.

The surface-active materials are generally present in an amount of 0.05 to 10%, preferably 0.5 to 5% by weight of the composition.

The tooth powders and pastes are prepared in the usual manner. Thus, the ingredients can be mixed in the dry state or as slurries or solutions.

In general the liquids in the dental cream or paste will comprise chiefly water, glycerine, sorbitol or propylene glycol, including suitable mixtures thereof. It is advantageous usually to use a mixture of water and glycerol, preferably in combination with sorbitol. The total liquid content will generally be 20 to 75% by weight of the preparation. It is preferred to use also a gelling agent in dental creams, such as natural or synthetic gums or gum-like materials, e.g. Irish Moss, gum tragacanth, sodium carboxymethylcellulose, polyvinylpyrrolidone or starch. Irish Moss and sodium carboxymethylcellulose are preferred gelling agents. The gum content is usually up to 10% and preferably 0.5 to 5% by weight of the preparation.

The pH of the dental cream or an aqueous slurry of the tooth powder is substantially neutral such as a pH of about 6 to 8. If desired, a small amount of acid such as citric acid or an alkaline material may be added.

Other materials may be added such as soluble saccharin, flavoring oils (e.g. oils of spearmint, wintergreen peppermint), chloroform, coloring or whitening agents (e.g. titanium dioxide), preservative (e.g. sodium benzoate), emulsifying agents, acidifying agents (e.g. citric acid), silicones, alcohol, menthol, chlorophyll compounds (e.g. sodium copper chlorophyllin), and antibacterial agents (e.g. chlorhexidine).

The compositions of the invention may also be in a form of other oral hygiene compositions, for example, the essential fluorine and calcium carbonate ingredients may be incorporated in mouth washes of the suspension type, or in compositions which will be chewed by the user, for example, chewing gum, tablets, pastilles and lozenges. These compositions will contain the conventional base materials together with suitable flavours and sweetening agents and may be formulated in known manner.

The compositions of the invention are illustrated by the following examples:

| FORMULATION | EXAMPLE | | | |
|---|---|---|---|---|
| | 1 | 2 | 3 | 4 |
| | (parts by weight) | | | |
| Glycerine | 25.0 | 12.5 | 25.0 | 12.5 |
| Sorbitol (70% Solution) | — | 12.5 | — | 12.5 |
| Sodium carboxymethylcellulose | 1.0 | 1.0 | 1.0 | 1.0 |
| Sodium Fluoride | 0.17 | 0.17 | 0.17 | 0.17 |
| Sodium Monofluorophosphate | 0.17 | 0.17 | 0.17 | 0.17 |
| Sodium lauryl sulphate | 1.5 | 1.5 | 1.5 | 1.5 |
| Sodium saccharin | 0.2 | 0.2 | 0.2 | 0.2 |
| Calcium carbonate | 45.0 | 45.0 | 45.0 | 45.0 |
| Calcium silicate | 0.20 | 0.20 | 0.20 | 0.20 |
| Flavour | 1.00 | 1.00 | 5.0 | 5.0 |
| Water | to 100% | to 100% | to 100% | to 100% |

The efficacy of the invention is illustrated by the following experiments carried out on the dissolution rate of hydroxyapatite. This is an appropriate model since it corresponds to the mineral composition of tooth enamel and is dissolved by the action of dilute acids such as those formed in the mouth from decaying food.

Discs of hydroxyapatite were prepared by blending it with 10% of polyethylene to improve binding characteristics followed by moulding separate discs by compression at 5000 kg. for 90 seconds and subsequent heating to 110°C. Separate discs were treated with a slurry of the dentifrice to be tested with water (water : dentifrice = 3 : 1) for one minute. The dentifrice composition had been stored for 2 weeks after its preparation and was of the general composition of that of Example 3, but wherein the ratio of sodium fluoride to sodium monofluorophosphate was varied while keeping the total fluorine concentration in the dentifrice uniform at a level of 1000 ppm (0.1% by weight of the total composition).

The treated hydroxyapatite discswere each placed beneath a rotating propeller in acetic acid buffer at pH 4.65 and 37°C for 1 hour. The percentage solubility reduction relative to treatment with an identical dentifrice but containing no fluorine was determined in each case. discs were results are set out in Table I below.

TABLE I

| NaF content % w/w of total fluorine | Content of F⁻ from NaF (ppm) | Content of F from $NaHPO_3F$ | Solubility reduction (%) |
|---|---|---|---|
| 0 | — | 1000 | 16.7 |
| 3.1 | 100 | 900 | 21.4 |
| 6.7 | 200 | 800 | 26.2 |
| 22.6 | 500 | 500 | 32.0 |
| 30.4 | 600 | 400 | 32.0 |
| 46.5 | 750 | 250 | 31.0 |
| 100 | 1000 | — | 23.8 |

These results show that when from 40–80% of the total fluorine content is provided by an alkali-metal fluoride, the solubility reduction effect on the hydroxyapatite is enhanced over the case where all the fluorine is provided by either an alkali-metal fluoride or by an alkali-metal monofluorophosphate. This effect is most enhanced when from 50 – 70% of the total fluorine content is provided by the alkali-metal fluoride.

In order to show that the inhibition in anticariogenic activity caused by the initial reaction of chalk and ionic fluoride can be overcome by adding small quantities of sodium fluoride to sodium monofluorophosphate, the following experiments were carried out according to the above described procedure using the composition of Example 3 with the fluoride/monofluorophosphate contents varied as shown. The results using a slurry of the composition in water (1 : 3) two minutes after preparation (Col. B) are compared with those from the effect of an aqueous solution of corresponding fluoride/monofluorophosphate content (Col. A).

TABLE II

| NaF concentration | Na Monofluorophosphate concentration | Total Fluoride concentration | % Reduction of solution A | % Reduction of slurry B |
|---|---|---|---|---|
| — | $5.0 \times 10^{-2}$ | $5 \times 10^{-2}$ | 36.0 | 29.5 |
| $1.1 \times 10^{-3}$ | $5.1 \times 10^{-2}$ | $5.2 \times 10^{-2}$ | 54.1 | 46.5 |
| $1.0 \times 10^{-2}$ | $4.1 \times 10^{-2}$ | $5.1 \times 10^{-2}$ | 50.9 | 47.1 |
| $1.6 \times 10^{-2}$ | $3.5 \times 10^{-2}$ | $5.1 \times 10^{-2}$ | 52.6 | 53.6 |

The above results indicate that by keeping the total fluoride level at $5.1 \times 10^{-2}$M or 1000 ppm in toothpaste, but increasing the proportion of sodium fluoride in a sodium fluoride/sodium monofluorophosphate mixture, then the initial reaction of fluoride with chalk can be overcome. This is shown by the convergence of activity as shown in columns A and B which shows that as the proportion of fluoride on the mixture increases so does the inactivation of the fluoride by the chalk (present only in the slurry) decrease.

We claim:

1. An oral hygiene composition comprising: (a) a calcium carbonate abrasive: (b) an ionic fluoride: and (c) an ionic monofluorophosphate, the weights of the said ingredients (b) and (c) being sufficient to provide respectively from 40–80% and 20–60% of the total fluorine content of the compositions.

2. An oral hygiene composition as claimed in claim 1 wherein ingredients (b) and (c) provide respectively 40–55% and 45–60% of the total fluorine content of the composition.

3. An oral hygiene composition as claimed in claim 1 wherein the total fluorine content is from 0.025% to 0.2% by weight of the composition.

4. An oral hygiene composition as claimed in claim 3 wherein the total fluorine content is from 0.05 to 0.12% by weight of the composition.

5. An oral hygiene composition as claimed in claim 1 in the form of a cored or striped dentifrice having an opaque core or stripes containing the calcium carbonate abrasive respectively enclosed within or laid upon a transparent gel.

6. An anti-cariogenic dentifrice having enhanced anti-cariogenic effect and comprising a polishing amount of calcium carbonate abrasive and a mixture of an ionic fluoride which produces fluoride ions in aqueous solution and an ionic monofluorophosphate, the fluoride and monofluorophosphate being present in the dentifrice in an amount to provide a total of from 0.025% to 0.2% of fluorine, based on the weight of the dentifrice, of which the fluoride provides 40–55% and the monofluorophosphate provides 45–60%.

7. An anti-cariogenic dentifrice according to claim 6 wherein the ionic fluoride is an alkali metal fluoride and the ionic monofluorophosphate is an alkali metal monofluorophosphate.

8. An anti-cariogenic dentifrice according to claim 7 wherein the ionic fluoride and the ionic monofluorophosphate are present in about equal proportions.

* * * * *

UNITED STATES PATENT OFFICE
CERTIFICATE OF CORRECTION

PATENT NO. : 3,966,863
DATED : June 29, 1976
INVENTOR(S) : Geoffrey Charles Forward et al It is certified that error appears in the above-identified patent and that said Letters Patent are hereby corrected as shown below:

<u>In the Abstract of the Disclosure</u> line 2, "carbide" should be --carbonate--.

Signed and Sealed this

Second Day of November 1976

[SEAL]

*Attest:*

RUTH C. MASON
*Attesting Officer*

C. MARSHALL DANN
*Commissioner of Patents and Trademarks*